(12) United States Patent
Biasiucci et al.

(10) Patent No.: US 10,046,161 B2
(45) Date of Patent: Aug. 14, 2018

(54) NEUROPROSTHETIC SYSTEM RESTORING UPPER LIMB FUNCTION THROUGH COORDINATED ELECTRICAL STIMULATION

(71) Applicant: Ecole Polytechnique Fédérale de Lausanne (EPFL), Lausanne (CH)

(72) Inventors: Andrea Biasiucci, Lausanne (CH); Andrea Maesani, Lausanne (CH); Hédi Dimassi, St-Germain (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 32 days.

(21) Appl. No.: 15/029,704

(22) PCT Filed: Oct. 17, 2014

(86) PCT No.: PCT/IB2014/065417
§ 371 (c)(1),
(2) Date: Apr. 15, 2016

(87) PCT Pub. No.: WO2015/059612
PCT Pub. Date: Apr. 30, 2015

(65) Prior Publication Data
US 2016/0303369 A1   Oct. 20, 2016

(30) Foreign Application Priority Data
Oct. 23, 2013   (WO) .................. PCT/IB2013/059574

(51) Int. Cl.
*A61N 1/00*   (2006.01)
*A61N 1/36*   (2006.01)
(Continued)

(52) U.S. Cl.
CPC ...... *A61N 1/36003* (2013.01); *A61B 5/04001* (2013.01); *A61B 5/04888* (2013.01);
(Continued)

(58) Field of Classification Search
CPC ...................... A61N 1/36003; A61N 1/04001
(Continued)

(56) References Cited

U.S. PATENT DOCUMENTS

| 4,558,704 A | 12/1985 | Petrofsky |
| 4,582,049 A | 4/1986 | Ylvisaker |

(Continued)

FOREIGN PATENT DOCUMENTS

| JP | 2002200104 A | 7/2002 |
| JP | 2013094305 A | 5/2013 |

OTHER PUBLICATIONS

Alon, Gad, Alan F. Levitt, and Patricia A. McCarthy. "Functional electrical stimulation enhancement of upper extremity functional recovery during stroke rehabilitation: a pilot study." Neurorehabilitation and neural repair 21.3 (2007): 207-215.
(Continued)

*Primary Examiner* — Nadia A Mahmood
(74) *Attorney, Agent, or Firm* — Andre Roland S.A.; Nikolaus Schibli

(57) ABSTRACT

Neuroprosthetic device for restoring daily-life action movements of upper limbs in patients suffering from motor impairments. The neuroprosthetic device comprises several non-invasive electrodes adapted to be fixed on a patient body, in a way as to stimulate at least two separate muscles which participate to the movement execution of the upper limb, an electrical stimulation device for injecting electrical current into said electrodes and a controller unit for regulating said currents through said electrodes. The neuroprosthetic device is characterized by the fact that the controller
(Continued)

unit comprises transducing means which are adapted to convert an input current. The input current is regulated according to the intention to execute a movement, into a plurality of electrical currents defined in a way as to generate and modulate the movement execution, in order to generate complex goal-oriented movements for performing daily-living activities.

18 Claims, 15 Drawing Sheets

(51) Int. Cl.
  *A61B 5/0488* (2006.01)
  *A61B 5/04* (2006.01)
  *A61N 1/04* (2006.01)
(52) U.S. Cl.
  CPC ......... *A61N 1/0452* (2013.01); *A61N 1/0492* (2013.01); *A61N 1/36014* (2013.01)
(58) Field of Classification Search
  USPC .......................................................... 607/48
  See application file for complete search history.

(56) References Cited

U.S. PATENT DOCUMENTS

| | | | |
|---|---|---|---|
| 5,167,229 | A | 12/1992 | Peckham et al. |
| 2002/0188331 | A1 | 12/2002 | Fang et al. |
| 2004/0015207 | A1* | 1/2004 | Barriskill ........... A61N 1/36003 607/49 |
| 2004/0023759 | A1 | 2/2004 | Duncan et al. |
| 2004/0044381 | A1 | 3/2004 | Duncan et al. |
| 2004/0147975 | A1 | 7/2004 | Popovic et al. |
| 2004/0267331 | A1 | 12/2004 | Koeneman et al. |
| 2007/0179560 | A1 | 8/2007 | Tong et al. |
| 2008/0147143 | A1 | 6/2008 | Popovic et al. |
| 2009/0062884 | A1 | 3/2009 | Endo et al. |
| 2009/0099627 | A1 | 4/2009 | Molnar et al. |

OTHER PUBLICATIONS

Chae, John, et al. "Neuromuscular stimulation for upper extremity motor and functional recovery in acute hemiplegia." Stroke 29.5 (1998): 975-979.
International Search Report (ISR) dated Jan. 20, 2015.
Langhorne, Peter, Fiona Coupar, and Alex Pollock. "Motor recovery after stroke: a systematic review." The Lancet Neurology 8.8 (2009): 741-754.
Pomeroy, Valerie M., et al. "Electrostimulation for promoting recovery of movement or functional ability after stroke." Cochrane Database Syst Rev 2 (2006).
Sirtori, Valeria, et al. "Constraint-induced movement therapy for upper extremities in stroke patients." Cochrane Database Syst Rev 4.4 (2009).
Taub, Edward, Jean E. Crago, and Gitendra Uswatte. "Constraint-induced movement therapy: A new approach to treatment in physical rehabilitation." Rehabilitation Psychology 43.2 (1998): 152.
Wolf, Steven L., et al. "Effect of constraint-induced movement therapy on upper extremity function 3 to 9 months after stroke: the EXCITE randomized clinical trial." Jama 296.17 (2006): 2095-2104.
Written Opinion of the International Search Authority dated Jan. 20, 2015.

* cited by examiner

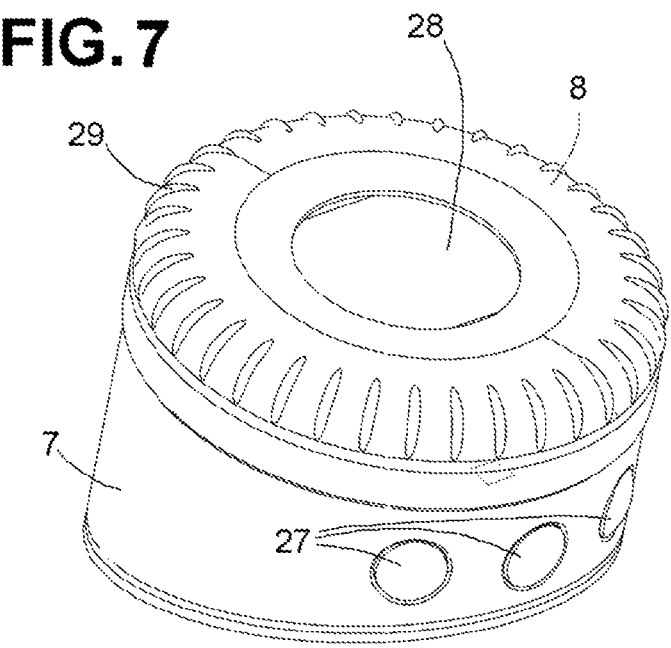

NEUROPROSTHETIC SYSTEM RESTORING UPPER LIMB FUNCTION THROUGH COORDINATED ELECTRICAL STIMULATION

The present application is a U.S. national stage application of PCT/IB2014/065417 filed on Oct. 17, 2014, and claims foreign priority to the Patent Cooperation Treaty (PCT) application PCT/IB2013/059574 filed on Oct. 23, 2013, the contents of both documents being herewith incorporated in their entirety.

FIELD OF INVENTION

The present invention relates to a neuroprosthetic device restoring daily-life actions involving upper limbs through electrical stimulation (ES). The present invention relates in particular to a neuroprosthetic device that allows continuous modulation of a movement according to the intention of the user to perform a certain action, extending the applicability of goal-oriented therapy and constraint-induced movement therapy to severely paralyzed patients.

BACKGROUND OF THE INVENTION

The loss of voluntary control of upper limb muscles is a widespread disability following central or peripheral nervous system lesions. The connection between the intention to perform an action and the coordinated contraction of muscles resulting in limb movements is lost. There is therefore the need to reconnect the intention of the user to the correct sequence of muscular contractions required to perform the movement.

Impaired individuals, such as stroke survivors or spinal cord injured patients, need to undergo long and intense physical rehabilitation sessions in order to recover, at least partially, the lost motor functions. Given the limited availability of resources in modern worldwide healthcare institutions, patients often receive insufficient amount of physical rehabilitation. In addition, a consistent number of patients never recover upper limb functionality even after massive therapy, developing a permanent disability. It is therefore a priority to develop methods and technological solutions aiming at improving the efficiency of the overall rehabilitation processes. To date, the most effective therapy for stroke rehabilitation is the constraint induced movement therapy (CIMT) (Langhorne et al. 2009).

CIMT for stroke rehabilitation is performed restraining the unaffected limb of a patient, for example using triangular bandages or a sling, therefore forcing the patient to an increased use of the affected limb. CIMT has proven its efficacy on patients with sufficient residual mobility (Wolf et al., 2006; Sirtori et al., 2009). However, this therapy cannot be applied on completely paralyzed patients. In fact, residual function is required to complete even the simplest tasks involving the unconstrained limb. Standard criteria for inclusion in CIMT require a patient to display 20 degrees of extension of the wrist and 10 degrees of extension of the fingers. Such relatively high level of motor ability is met by less than 50% of stroke patients (Taub et al., 1998).

Current motor rehabilitation also relies on intensive exercise sessions, robotic rehabilitation systems or peripheral electrical stimulation of nerves and muscles. Intensive exercise sessions are usually limited by the availability of therapist time. Robotic solutions are developed to replace therapists in intensive exercises sessions. However, robotic solutions are still expensive and a limited number of units can be afforded by hospitals, if any. Most importantly, existing robotic solutions (such as InMotion ARM™, Hocoma Armeo™, etc.) only provide passive means of exercising, helping to displace patient's limbs, and are of limited use for completely paralyzed individuals.

Neuroprosthetic devices have the potential of both improving current rehabilitation, by increasing therapy time, and restoring function in permanently disabled individuals. This invention relates to a neuroprosthetic system that allows patient to generate goal-oriented movements of their paralyzed limb. Embodiments of the invention could be used to perform constraint-induced movement therapy on severely paralyzed patients by actuating patient's muscles through neuromuscular electrical stimulation.

Electrical stimulation of upper limbs has shown promising results in promoting voluntary upper limb function recovery (Chae et al., 1998; Alon et al., 2007; Pomeroy et al., 2009). However, in the current medical practice, electrical stimulation therapy is limited by the availability of skilled clinicians in the art and by the lack of a general consensus on how to maximize its efficacy.

Various systems providing electrical stimulation therapy to restore upper limb functions have been proposed. Generally, such systems comprise several invasive or surface electrodes to convey electricity from an electrical stimulator to nerves and muscles of a user. A controller unit generates the electrical current signals Such electrical current is produced according to a predefined sequence of stimulation, or willingly by users.

Several systems to restore upper limb functionality rely on electrodes implanted in the limb to deploy electrical stimulation such as the systems disclosed in Peckham et al., 1992 (U.S. Pat. No. 5,167,229), and in Fang et al., 2002 (US 2002/0188331). Both systems are controlled either by an implanted or external shoulder joystick operated by the user.

Implanting the electrodes solves the problem of maintaining them placed on a specific stimulation site, but requires an expensive and risky surgery. Other systems use surface electrodes, solving the issue by mounting the electrodes on arms-mounted orthosis such as Tong et al., 2007 (US 2007/0179560) or Koeneman et al., 2004, (US 2004/0267331). However, such orthosis are usually very bulky, limiting user mobility, and cannot ensure optimal contact while performing movements, i.e. relative positions and contact area of electrodes and skin changes during use.

Other proposed systems employ cheap surface electrodes, attached to the skin through adhesive conductive glue such as Popovic et al., 2004 (US 2004/0147975). However, the use of surface electrodes requires expert help for positioning said electrodes. Moreover, such standard electrodes are not adapted to guarantee stable positioning over the skin during movements. Most importantly, the glue deteriorates as time goes by favoring detachment of electrodes resulting in discomfort and pain by the users.

Other solutions such as Petrovsky, 1985 (U.S. Pat. No. 4,558,704) addresses only specific functionality of the upper limbs, namely hand opening and closing.

All the above cited systems either allow: 1) simply enabling or disabling the stimulation by use of a switch or button, without providing any means to modulate the stimulation; or 2) modulating the stimulation (and therefore the resulting movement) by providing to the user non-intuitive means to generate a control signal, such as shoulder joysticks. Therefore, they are not suitable to be operated by elderly or cognitive disabled individuals.

A recent system disclosed by Molnar et al., 2009 (US 2009/0099627) describes a system that decodes a movement state directly from the brain of a patient and deliver a therapy accordingly. However, the system requires either implanted electrodes or relies on standard surface electrodes, incurring in the aforementioned problems of maintaining optimal placement.

There is therefore the need to develop a neuroprosthetic device that can be used both as a rehabilitation and assistive technology tool to restore daily life activities involving upper limbs, providing intuitive means to modulate the movements. Moreover, such device should provide easy application of electrodes and ensure electrode placement for long period of time. Finally, to integrate the device into current medical practice it should provide means to improve and extend constraint-induced movement therapy to any type of paralyzed patient.

Scientific references

Sirtori V, Corbetta D, Moja L, Gatti R, "*Constraint-induced movement therapy for uppper extremities in stroke patients*", Cochrane Database Systematic Review, 2009.
Wolf S L, Winstein C J, Miller J P, Taub E, Uswatte G, Morris D, Giuliani C, Light K E, Nichols-Larsen D, "*Effect of constraint-induced movement therapy on upper extremity function 3 to 9 months after stroke*", JAMA, 2006.
Taub E, Crago J E, Uswatte G, "*Contraint-induced movement therapy: A new approach to treatment in physical rehabilitation*", Rehabilitation Psychology, 1998.
Pomeroy V M, King L M, Pollock A, Baily-Hallam A, Langhorne P, "*Electrostimulation for promoting recovery of movement or functional ability after stroke*" Cochrane Database Systematic Review, 2009.
Alon G, Levitt A F, McCarthy P A, "*Functional Electrical Stimulation Enhancement of Upper Extremity Functional Recovery During Stroke Rehabilitation: A Pilot Study*", Neurorchabilitation and neural repair, 2007.
Chae J, Bethoux F, Bohinc T, Dobos L, Davis T, Friedl A, "*Neuromuscular Stimulation for Upper Extremity Motor and Functional Recovery in Acute Hemiplegia*" Stroke 1998.
Langhorne P, Coupar F, Pollock A. "*Motor recovery after stroke: a systematic review*". The Lancet Neurology, 2009.

SUMMARY OF THE INVENTION

An aim of the invention is thus to provide a non-invasive device that restores daily life actions involving a paralyzed upper limb.

This aim is achieved in particular by a neuroprosthetic device comprising several non-invasive electrodes adapted to be fixed on the body of the user. This device also comprises an electrical stimulation unit for generating electrical currents that flow through aforementioned electrodes causing muscular contractions and a controller unit for regulating said currents. This controller unit comprises an intention transducing unit which is adapted to convert an input current, regulated according to the intention of the user to execute the desired action, into a plurality of electrical currents being defined in a way as to generate and modulate limb movements, accordingly. Importantly, said movements are goal-oriented, and can restore basic activities of daily living and goal-oriented tasks. Furthermore the controller unit is adapted to generate electrical currents that mitigate muscular fatigue when the device is not actively operated by the user.

A second aim of the invention is to provide a neuroprosthetic device allowing an easy implementation of the constraint-induced movement therapy for partially or completely paralyzed patients.

This aim is achieved in particular by a neuroprosthetic device comprising a constraining orthosis blocking the healthy limb adapted to sustain and allow easy attachment and detachment of the controller and stimulating units.

A third aim of the invention is to provide an intuitive device that can be easily operated by elderly or cognitively impaired individuals.

This aim is achieved in particular by a neuroprosthetic device that transduces the intention to perform a certain action into a one dimensional control variable for the controller unit. The intention can be transduced by a variety of means such as the rotation of a knob, electromyography signal extracted from a body part, touch sensors located in contact with a finger of the user, eye movements or body tracking systems. The neuroprosthetic device is characterized by the fact that for a given action the modulation of movement is achieved through modulation of said one dimensional control variable.

A fourth aim of the invention is to provide an easy to mount device that is well adapted to fit the morphology of the user, thus increasing the comfort of usage.

This aim is achieved in particular by embedding multiple electrodes into adhesive supports, thus minimizing the number of operations required to correctly place the electrodes on the limbs. Also, the wires connecting each electrode to the stimulation unit are grouped into a single flexible wire running through the different adhesive supports, thus avoiding dangling cables. The adhesive supports can be easily placed through the aid of a semi-rigid orthosis, acting as a user-customized placement system. Another way in which this aim can be achieved is by using means to deposit a layer of conductive polymer on the skin of the patient, allowing therapist to "draw" custom electrodes on the patient's skin. Such conductive polymer can cure (solidify) in a relatively fast time and be easily detached if needed from the skin, for example being washable. The polymer can be applied for example by a marker.

A fifth aim of the invention is to provide a neuroprosthetic device that can replicate movements of a limb of other users, enabling parallel reproduction of movements on several devices or allowing mirror therapy on the same user This aim is achieved in particular by a neuroprosthetic device comprising a controller unit adapted to receive wirelessly stimulation commands.

BRIEF DESCRIPTION OF THE DRAWINGS

The present invention will be better understood with the help of the following description illustrated by the figures, wherein:

FIG. 7 shows an intention transducing unit in the form of a rotating knob, according to an embodiment of the invention.

FIG. 14 shows a fast curing conductive polymer being applied using a suitable marker on the skin of a user.

LIST OF FIGURE LABELS

Figure 1:
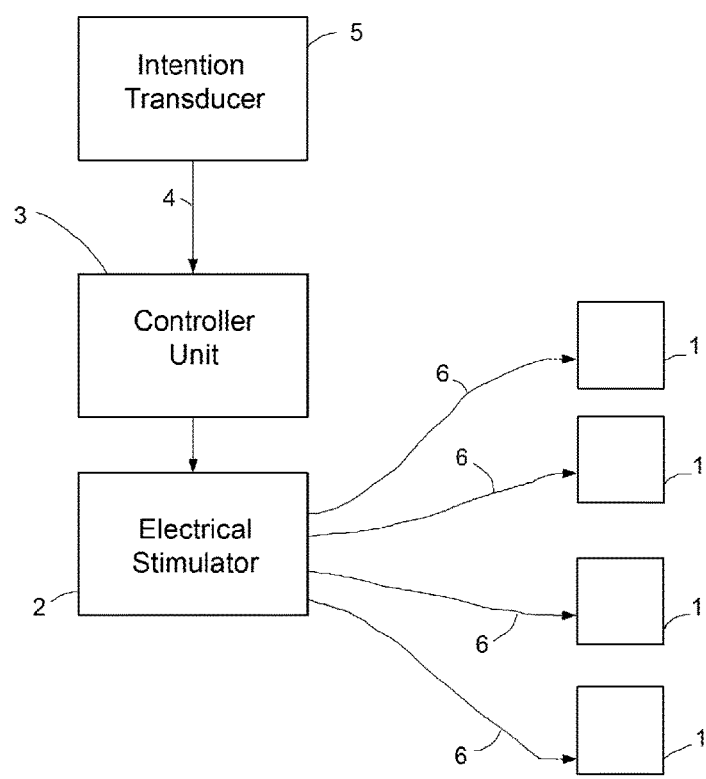
FIG. 1 shows a simplified block diagram of one embodiment of the invention.

1. Electrodes
2. Electrical stimulator
3. Controller unit
4. Input signal
5. Intention transducer
6. Plurality of electrical currents
7. Cylindrical casing
8. Rotating knob
9. Constraint orthosis
10. Docking station
11. Electrode adhesive patch
12. Other casing
13. Master controller
14. 3d camera based tracking system
15. Target user
16. Available users in range
17. Finger mounted intention detector
18. EMG bracelet
19. Electrode attachment plug
20. Conductive area
21. Adhesive support with multiple electrodes
22. Multi-channel plug for connection with other patches
23. Wiring
24. Movement Controller and constraint
25. Arm Braces
26. Locking mechanism
27. Buttons
28. Screen
29. Knob parts in relief
30. Biceps brachii
31. Brachialis
32. Flexor digitorum superficialis
33. Narrow adhesive section
34. Extensor indicis proprii
35. Subspinous fossa
36. Pectoral minor
37. Pectoral major
38. Deltoid
39. Flexor pollicis longus
40. Fast curing polymer with conductive particles
41. Marker
42. Lead to electrical stimulator
43. Adjustable length part
44. electrode biceps
45. electrode flexor digitorum superficialis
46. electrode distal extensor indicis proprium
47. electrode proximal extensor indicis proprium
48. electrode distal subspinous fossa
49. electrode proximal subspinous fossa
50. electrode proximal flexor digitorum superficialis
51. electrode distal pectoral minor
52. electrode ventral pectoral major
53. electrode ventral portion deltoid
54. electrode lateral proximal deltoid
55. electrode distal flexor pollicis longus
56. electrode distal ventral flexor digitorum superficialis
57. electrode distal extremity deltoid
58. distal pectoralis major
59. ventral distal deltoid
60. Buttons on hand worn controller
61. Rotating knob on hand worn controller
62. Generic stimulation or sensing connection wire
63. Generic stimulation or sensing multi-channel plug

DETAILED DESCRIPTION OF THE INVENTION

FIG. 1 shows the simplified block diagram of the neuroprosthetic device comprising several non-invasive electrodes 1, an electrical stimulation unit 2 and a controller unit 3 adapted to convert an input current 4 generated by an intention transducer unit 5 into a plurality of electrical currents 6. The controller unit 3 internally processes the input current 4 converting it into stimulation commands for the electrical stimulator 2, said stimulator eventually generating a plurality of electrical current 6.

Figure 2A:
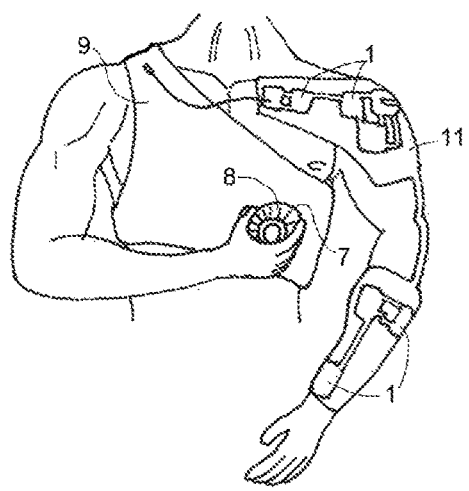
FIGS. 2A, 2B and 2C shows the neuroprosthetic device according to a preferred embodiment of the invention.

In a preferred embodiment, illustrated in FIG. 2a, the neuroprosthetic device comprises a cylindrical casing 7 fixed on a rigid, semi-rigid or soft orthosis 9. The cylindrical casing 7 embeds the electrical stimulator 2, the controller unit 3 and an intention transducing unit 5 in the form of a rotating knob 8, fixed on top of the cylindrical casing 7.

The preferred embodiment illustrated in FIG. 2a allows delivering constraint-induced movement therapy to users of the neuroprosthetic device, thus providing a device for performing a therapy that we named 'electrically-assisted constraint-induced movement therapy' (EA-CIMT).

Constraint-induced movement therapy is a rehabilitation approach mainly used for brain stroke survivors. Concerning upper limbs, it consists in immobilizing the healthy side of the body therefore forcing patients to train their affected side through exercises. This therapy requires a certain degree of residual movement in the impaired limb, and currently cannot be performed on completely paralyzed patients. EA-CIMT overcomes this limitation by allowing patients, even completely paralyzed, to control movements of the affected side of the body with the healthy side of the body. The fact that physical movement controllers are operated using the healthy limb, for example with the unaffected hand, implies that such devices serve both as movement controllers and as constraining means.

The preferred embodiment of FIG. 2a allows delivering EA-CIMT to completely paralyzed patients, even immediately after the stroke.

The ergonomics of the cylindrical casing 7 facilitates knob rotation by a constrained healthy limb. Moreover, choosing a knob as an intention transducing unit allows intuitive interaction also by elderly people.

Figure 2B:
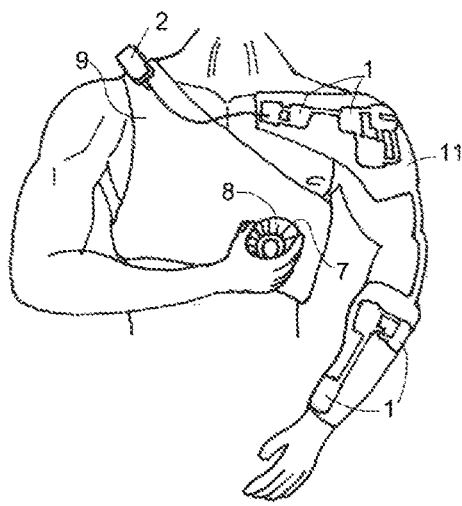

In another preferred embodiment, illustrated in FIG. 2b, the cylindrical casing 7 only embeds the controller unit 3 while the electrical stimulator 2 is docked to another supporting structure of the orthosis.

To accommodate weight or space limitations defined by the application, the controller unit 3 and/or the electrical stimulator 2 can be embedded together or not in the cylindrical casing 7.

Figure 2C:
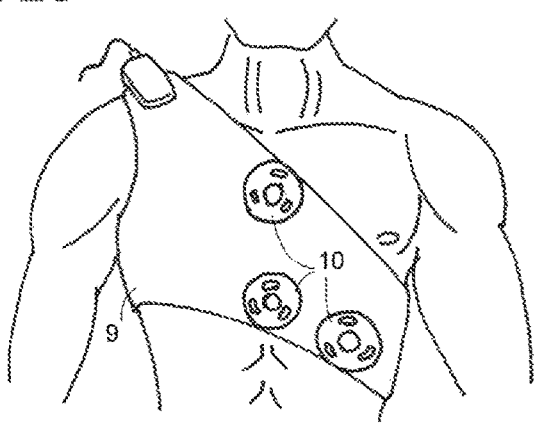

FIG. 2c shows the orthosis 9 without any attached cylindrical casing. The orthosis 9 allows easy attachment and detachment of the cylindrical casing 7 by means of the docking means 10. As illustrated in FIG. 2b, the orthosis 9 can be adapted to embed several docking means 10, allowing the customization of the position of the cylindrical casing 7 according to user comfort.

Figure 3:
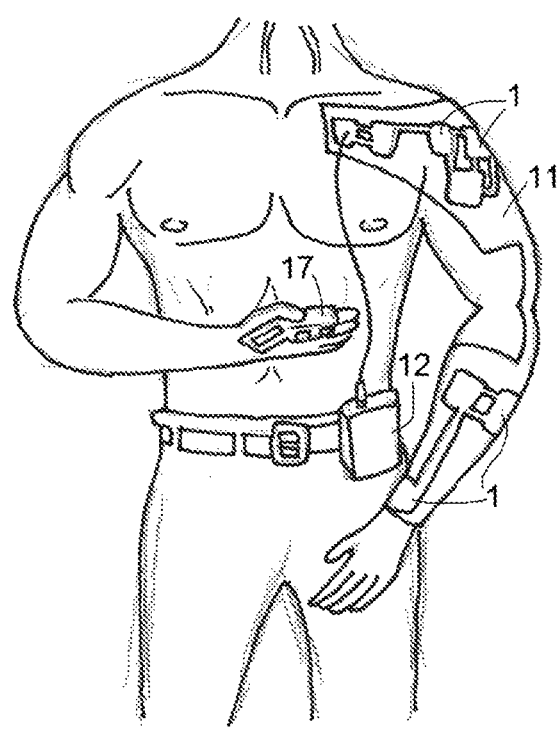
FIG. 3 shows the neuroprosthetic device according to another preferred embodiment of the invention.

In a preferred embodiment, illustrated in FIG. 3, the neuroprosthetic device comprises the casing 12, adapted to be worn on the body, which includes the electrical stimulator 2, the controller unit 3 and means adapted to communicate wirelessly with an intention transducing unit 5 in the form of a finger mounted touch sensitive device 17.

One of the current problems of wearable devices is their intrusiveness and visibility, resulting in reduced comfort and ease-of-use. The intention transducer unit 5 in the form of a finger mounted touch sensitive device 17 is therefore designed to be worn on a single finger, preferably the index, and operated with another finger, preferably the thumb. In addition, the choice of device ergonomics, colors and materials is made in order to minimize intrusiveness and visibility.

Figure 4:
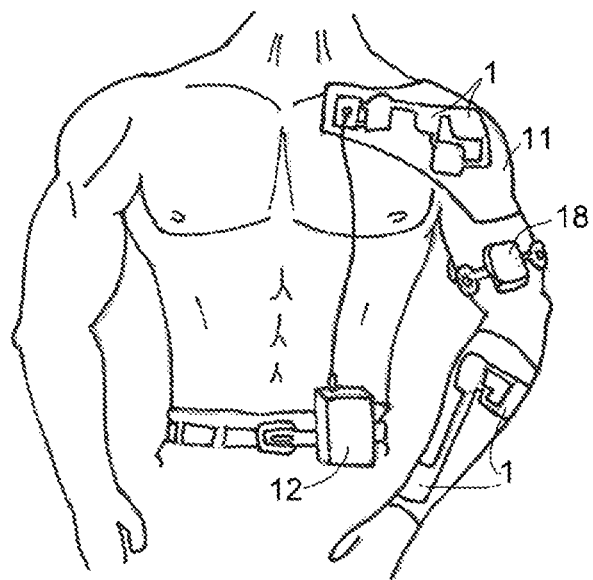
FIG. 4 shows the neuroprosthetic device according to another preferred embodiment of the invention.

In another preferred embodiment, illustrated in FIG. 4 the intention transducer unit 5 has the form of an arm mounted device 18 to record and process electromyography signals.

The forearm mounted device 18 is minimally intrusive and allows fine object manipulation in patients having residual muscular activity in the forearm, thus optimizing ease-of-use.

Using residual muscular activity in the arm or forearm, decoded through the arm mounted device 18, is of special interest for rehabilitation settings, since an automatic system can be adapted to reinforce beneficial muscular patterns and discard abnormal responses while trying to accomplish a certain action. Arm mounted device 18 can be placed on different positions of the arm and the forearm in order to record EMG activity of different muscle groups, accommodating specific patient's needs.

Figure 5:
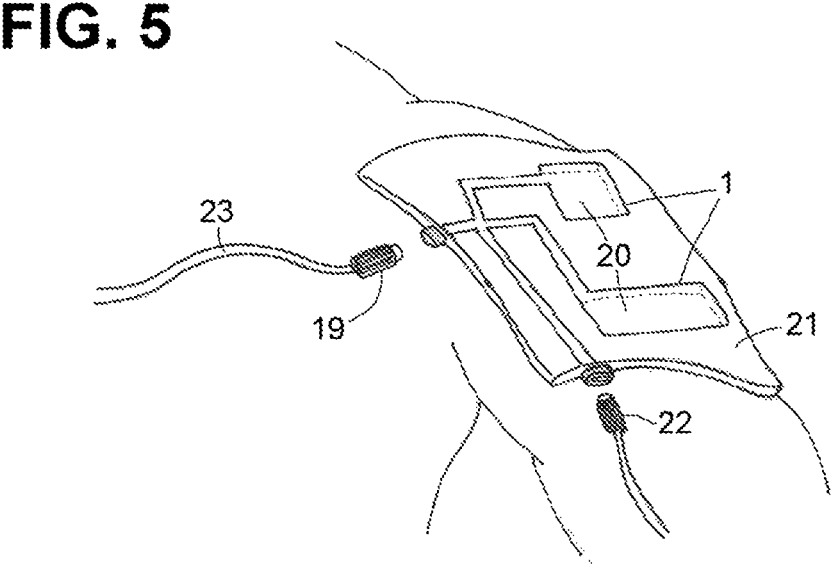
FIG. 5 shows an electrode support according to an embodiment of the invention.

As illustrated in FIG. 5, the conductive surface 20 of electrodes 1 is in contact with the skin of the user. Electrodes 1 are grouped onto an insulating adhesive support 21 embedding multiple electrodes 1. Electrodes 1 are connected through a multi-channel plug 19 to the electrical stimulator 2, through the wiring 23.

Grouping the electrodes into a single disposable support 21 allows easy and fast replacement of multiple electrodes, minimizing the time needed to setup the neuroprosthetic device on a user.

Adhesive support 21 can be produced in different sizes in order to accommodate a variety of upper limb morphologies. In addition, electrodes 1 are placed on the supports in pre-defined positions in order to allow the generation of the desired set of actions.

The multi-channel plug 19 allows easy connection of all the electrodes 1 to the electrical stimulator 2, minimizing montage time. Furthermore every disposable support can be connected by means of other multi-wire plugs 22 to electrodes on different adhesive supports.

The preferred embodiments of FIG. 6 facilitate prolonged EA-CIMT on paralyzed patients.

Figure 6A:
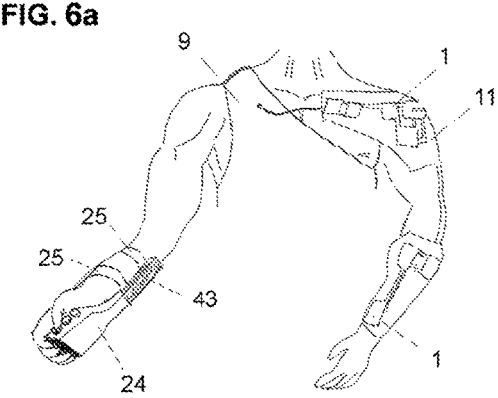
FIG. 6 shows the neuroprosthetic device according to another preferred embodiment of the invention allowing electrically-assisted constraint-induced movement therapy.

FIG. 6a illustrates an intention transducer unit 5 in the form of a wearable controller 24 that is fixed on the healthy limb through forearm-mounted braces 25. The rigid orthosis 9 is adapted to embed wiring and allow the placement of electrodes on the patient's back. Moreover, the orthosis contains the wiring necessary to provide electrical connectivity between the wearable controller 24 and the electrodes 1, which are embedded into a supporting adhesive patch 11. Said adhesive patch 11 maintains the system in the desired positions and includes wiring to connect the electrodes.

In another preferred embodiment, the wearable controller 24 communicates wirelessly with at least one electrical stimulator 2 wired to stimulation electrodes 1.

Figure 6C:
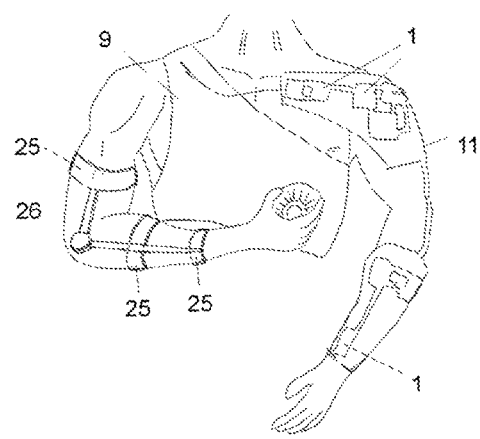
Figure 6B:
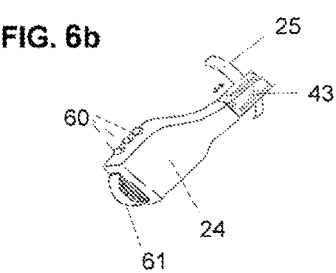

FIG. 6b illustrates an embodiment of the wearable movement controller 24 having forearm-mounted braces 25, and adjustable length in order to be fixed on patients having different forearm length. Furthermore, the part with adjustable length 43 allows the user to displace the movement controller 24, freeing the healthy hand for use. Said wearable movement controller 24 has buttons 60 that allow users to select the desired movement with the thumb and a rotating knob 61 that allows users to modulate the selected movement according to their will. Said rotating knob 61 acts as rotating knob 8 shown in FIGS. 2a and 2b.

FIG. 6c illustrates an embodiment where the healthy arm weight is supported through a locking system 26 adapted to mechanically stabilize the relative angle between the proximal and distal portions of the arm. Said locking system 26 is fixed to the body through arm-braces 25.

The rigid orthosis 9 and locking system 26 are adapted to constrain and to support the healthy limb, thus avoiding postural fatigue. Moreover, the orthosis internally contains the appropriate wiring to provide electrical connectivity between the wearable controller 24 and the electrodes 1, which are embedded into a supporting adhesive patch 11 that maintains the electrodes in the desired positions and includes wiring to connect the electrodes.

Figure 6D:
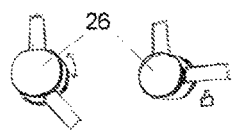

FIG. 6d further illustrates an embodiment of a 2-states adjustable locking mechanism 26 either allowing rotations of the elbow joint or providing mechanical support against gravity.

FIG. 7 illustrates how the intention transducing unit 5, in the form of a rotating knob 8, is embedded into a cylindrical casing 7 comprising the controller unit 3. Said rotating knob 8 was also illustrated in FIG. 2a, 2b, 6c.

Buttons 27 located on the side walls of the cylindrical casing 7 allow the user to select the desired action. Buttons 27 also allows switching on and off the device and select additional functionalities offered by the device and visualized on the screen 28.

The rotation of knob 8 is transformed into an electrical signal by means of a mechanical to electrical signal transducer, for example a rotary encoder, magnetic encoder or optical device. Such signal is transmitted to the controller unit 3.

The knob 8 can include parts in relief 29 to facilitate handling and rotation of the knob, especially for elderly users.

The controller unit 3 is connected to an internal or external electrical stimulator 2. In the case of embedding an internal electrical stimulator 2 the controller unit 3 is connected through a multichannel plug to the electrodes 1.

The intention transducing unit 5 provides connectivity to external devices through wires or wirelessly.

The intention transducing unit 5 is powered by a rechargeable battery embedded in the cylindrical casing 7. The battery can be recharged through the power plug.

The controller unit 3 comprises a microcontroller or microprocessor to perform internal computation and drive the electrical stimulator 2, transforming signals received from intention transducing unit 5 to input signals for the electrical stimulator 2.

Figure 8A:
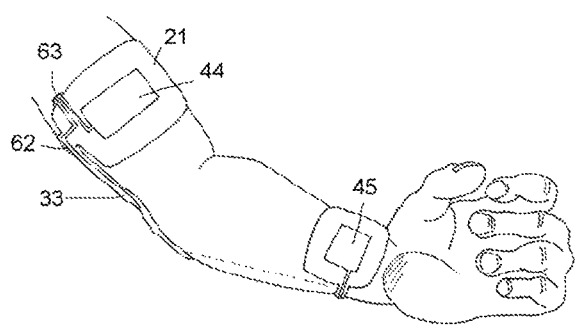
FIG. 8a shows the electrode support montage resulting in one of the actions provided by one of the embodiments of the invention.

FIG. 8*a* illustrates an electrodes support 21 manufactured to embed and correctly place on the body electrodes 44 and 45.

Figure 8B:
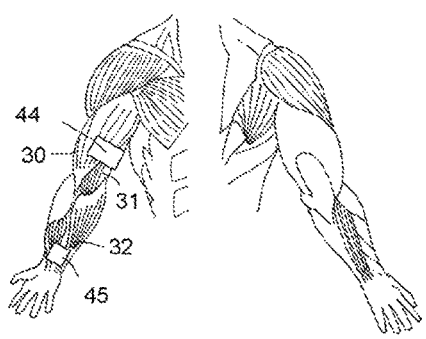
FIG. 8b shows a detailed view of the muscles involved during the electrical stimulation and FIGS. 8c, 8d and 8e shows the action produced by the stimulation.

FIG. 8*b* clarifies the muscles electrically stimulated by the electrodes embedded in adhesive support 21. Electrode support 21 is adapted to maintain electrode 44 fixed on top of the ventral, proximal side of the biceps brachii muscle 30, also involving the brachialis muscle 31 (to obtain elbow flexion and supination); and electrode 45 on the distal extremity of the flexor digitorum superficialis muscle 32 (to obtain fingers flexion and palmar hand grasping). Electricity is injected through bipolar montage over electrodes 44 and 45 as to jointly stimulate biceps and fingers flexor muscles.

Figure 8C:
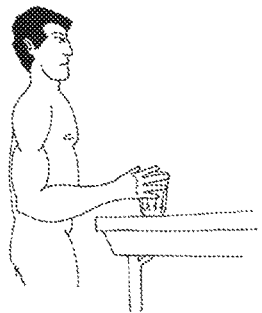
Figure 8D:
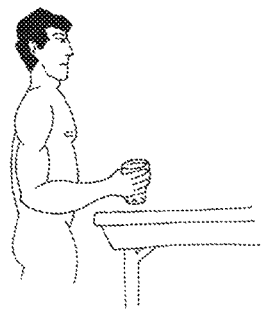
Figure 8E:
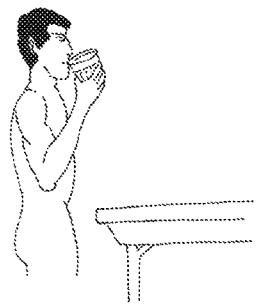

Electrodes 44 and 45 allow stimulation with electrical currents, for example with a rectangular waveform, wherein said waveform has a frequency between 15 and 60 Hz, a pulse width between 150 and 500 us and a current intensity between 0 and 50 mA to induce harmonious movement to grasp and bring objects located in front of the body to the mouth, as shown in FIG. 8*c* (starting position), FIG. 8*d* (intermediate position) and FIG. 8*e* (final position).

The electrical connectivity between electrodes 44 and 45 is ensured by a generic stimulation or sensing connection wire 62 embedded into the adhesive support 21.

Electrode support 21 comprises a narrow adhesive section 33 running on the posterior side of the forearm, over the line defined by the ulna bone connecting the elbow to the wrist joints.

Adhesive section 33, maintaining the generic stimulation or sensing connection wire 62 attached to the arm, prevents it from being unwillingly pulled during the execution of daily life actions.

The support can be connected to the electrical stimulator 2 by means of a generic stimulation or sensing multi-channel plug 63.

Figure 9A:
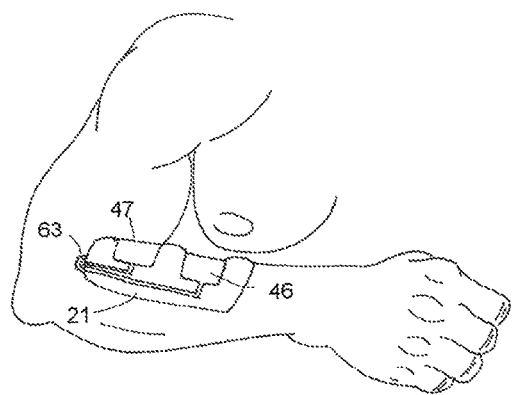
FIG. 9a shows the electrode support montage resulting in one of the actions provided by one of the embodiments of the invention.

FIG. 9*a* illustrates an electrodes support 21 manufactured to embed and correctly place on the body electrodes 46 and 47.

Figure 9B:
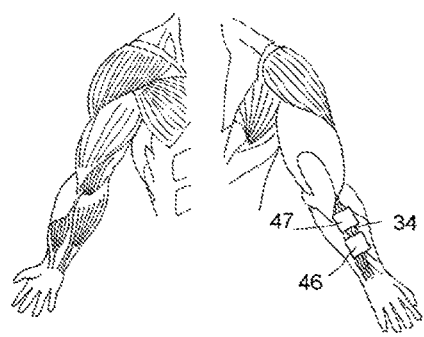
FIG. 9b shows a detailed view of the muscles involved during the electrical stimulation and FIGS. 9c and 9d shows the action produced by the stimulation.

FIG. 9*b* clarifies the muscles electrically stimulated by the electrodes embedded in support 21. Electrodes support 21 is adapted to maintain electrode 47 on the proximal extremity of the extensor indicis proprium muscle 34 and electrode 46 on the distal extremity of the extensor indicis proprium muscle 34 (to obtain index extension). Electricity is injected through bipolar montage over electrodes 46 and 47 as to stimulate the extensor indicis proprium muscle.

Figure 9C:
Figure 9D:

Electrode 46 and 47 allow stimulation with electrical currents, for example with a rectangular waveform, wherein said waveform has a frequency between 15 and 60 Hz, a pulse width between 150 and 500 us and a current intensity between 0 and 40 mA to induce harmonious movement to extend the index and point at objects located everywhere in space. For example FIG. 9*c* shows the starting position of the action and FIG. 9*d* the ending position resulting in the execution of the action.

Figure 10A:
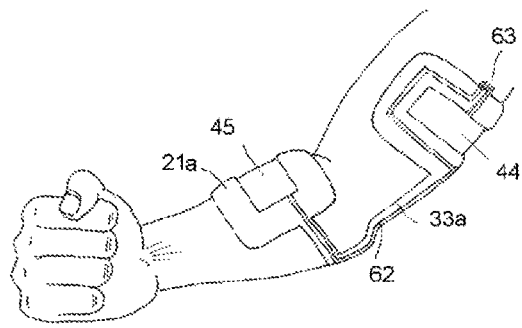
FIGS. 10a, 10c and 10d shows the electrode support montage resulting in one of the actions provided by one of the embodiments of the invention.
Figure 10B:
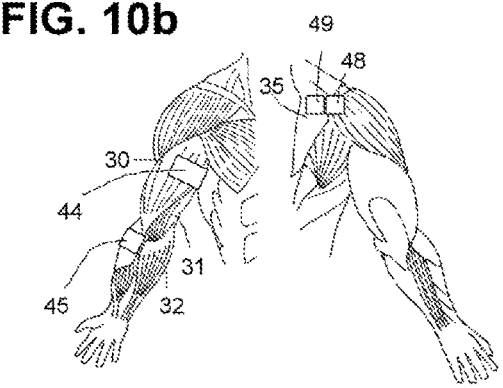
FIG. 10b shows a detailed view of the muscles involved during the electrical stimulation.
Figure 10C:
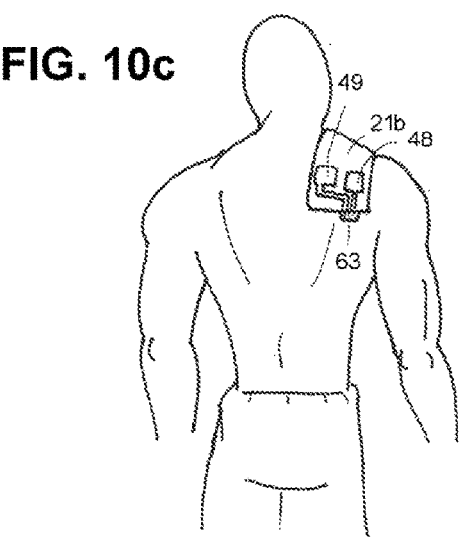
Figure 10D:
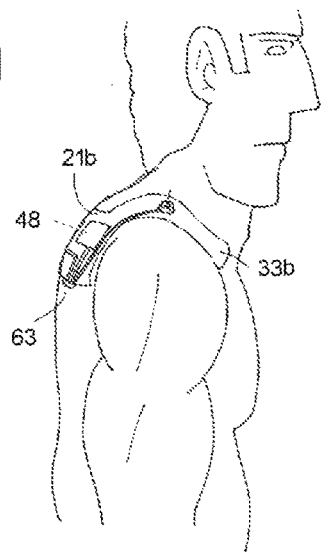

FIGS. 10*a*, 10*c* and 10*d* illustrate electrode supports 21*a* and 21*b* manufactured to embed and correctly place on the body electrodes 44, 45, 48, 49.

FIG. 10*b* clarifies the muscles electrically stimulated by the electrodes embedded in support 21*a*. One electrode support 21*a* is adapted to maintain electrode 44 on the ventral, proximal side of the biceps brachii muscle 30, also involving the brachialis muscle 31 (to obtain elbow flexion and supination) and electrode 45 on the flexor digitorum superficialis muscle 32 (to obtain fingers flexion and palmar hand grasping). Electricity is injected through bipolar montage over electrodes 44 and 45 as to separately stimulate the biceps and fingers flexor muscles.

Another electrode support 21*b* is adapted to maintain electrode 48 on the distal extremity of the sub spinous fossa 35 and another electrode 49 on the proximal extremity of the sub spinous fossa 35 (to obtain external shoulder rotation). Electricity is injected through bipolar montage over electrodes 48 and 49.

Electrodes 44 and 45 allow stimulation with electrical currents, for example with a frequency between 15 and 60 Hz, a pulse width between 150 us and 500 us and a current intensity between 0 and 50 mA.

Electrodes 48 and 49 allow stimulation with electrical currents, for example with a frequency between 15 and 60 Hz, a pulse width between 150 us and 500 us and a current intensity between 0 and 60 mA.

Figure 10E:
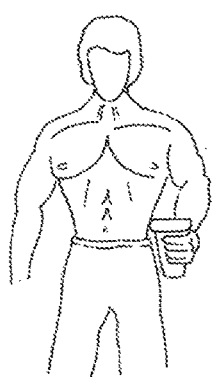
FIGS. 10e and 10f shows the action produced by the stimulation.
Figure 10F:
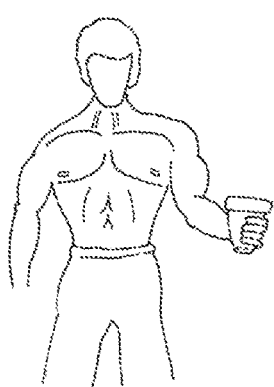

The electrical parameters of currents applied on electrodes 44, 45, 48, 49 are designed to induce harmonious movement to pass objects from a position in front of the body to a position far from the body, on the same hemi-space of the stimulated limb as shown in FIG. 10*e* (starting position) and FIG. 10*f* (final position).

Electrode supports 21*a* might comprise a narrow adhesive section 33*a* running on the posterior side of the elbow between the lateral epicondyle and the olecranon.

Adhesive section 33*a*, maintaining the generic stimulation or sensing connection wire 62 attached to the arm, prevents it from being unwillingly pulled during the execution of daily life actions.

Electrode support 21*b* might comprise an elongated adhesive portion 33*b* running over the acromion stabilizing support 21*b* and allowing prolonged usage during the day.

Electrical connectivity between the electrical stimulator 2 and the electrodes support 21*a* is allowed by wiring connected to generic stimulation or sensing multi-channel plug 63*a*. Electrical connectivity to the electrode support 21*b* is established by connecting the generic stimulation or sensing multi-channel plug 63*b* by means of proper wiring.

Figure 11A:
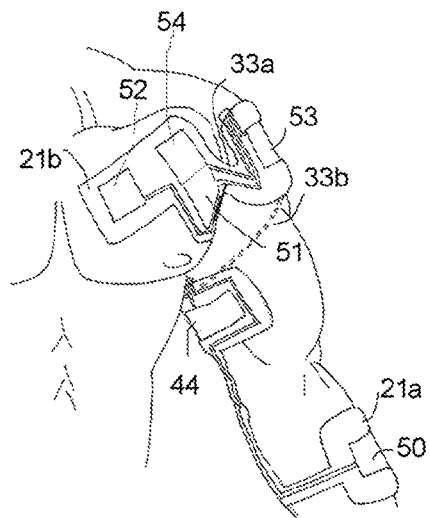
FIG. 11a shows the electrode support montage resulting in one of the actions provided by one of the embodiments of the invention.

FIG. 11*a* illustrates electrode supports 21*a* and 21*b* manufactured to embed and correctly place on the body electrodes 44, 50, 51, 52, 53, 54.

Figure 11B:
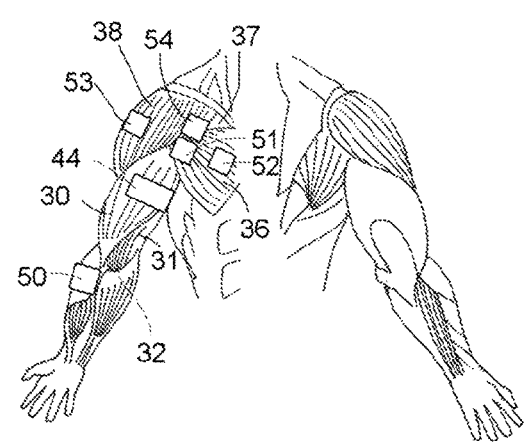
FIG. 11b shows a detailed view of the muscles involved during the electrical stimulation and FIGS. 11c and 11d shows the action produced by the stimulation.

FIG. 11*b* clarifies the muscles electrically stimulated by the electrodes embedded in supports 21*a* and 21*b*. One Electrode support 21*a* is adapted to maintain electrode 44 on the ventral, proximal side of the biceps brachii muscle 30, also involving the brachialis muscle 31 (to obtain elbow flexion and supination) and another electrode 50 on the lateral side of the on the flexor digitorum superficialis muscle 32 (to obtain fingers flexion and palmar hand grasping). Electricity is injected through bipolar montage over electrodes 44 and 50 as to jointly stimulate the biceps and fingers flexor muscles.

Another electrode support 21b is adapted to maintain electrode 51 on the distal extremity of the pectoralis minor 36, electrode 52 on the ventral portion of the pectoralis major 37 in correspondence of the ventral part of the underlying pectoralis minor 36 (to obtain internal shoulder rotation and arm flexion crossing the median plane), electrode 53 on the ventral portion of the deltoid muscle 38 and electrode 54 on the lateral proximal side of the deltoid muscle 38, below the clavicle (to support internal shoulder rotation and arm flexion on the median plane). Electricity is injected through a bipolar montage over electrodes 51, 52 and 53, 54 as to separately stimulate the pectoralis and deltoid muscles.

Electrodes 44, 50, 51, 52, 53, 54 allow stimulation with electrical currents, for example with a rectangular waveform, wherein said waveform has a frequency between 15 and 60 Hz, a pulse width between 150 us and 500 us and a current intensity between 0 to 60 mA.

Figure 11C:
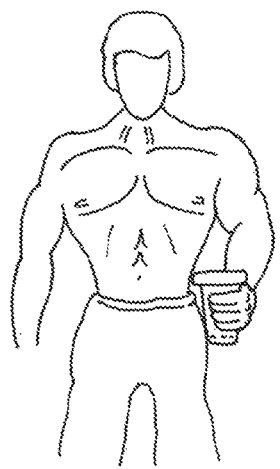
Figure 11D:
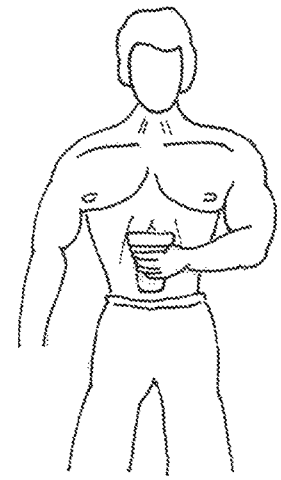

The electrical parameters of currents applied on electrodes 44, 50, 51, 52, 53, 54 are designed to induce a harmonious movement to pass objects from a position in front of the body to a position far away towards the opposite side of the body as shown in FIG. 11c (starting position) and FIG. 11d (final position).

Electrode support 21a comprises one narrow adhesive section 33a running from the pectoralis major 37 towards the shoulder. Adhesive section 33a has a shape adapted to fit and hold to the clavicle, ensuring that the placement of electrode support 21a is stable during complex movements.

Another electrode support 21b comprises one narrow adhesive section 33b running from the shoulder to the armpit. Adhesive section 33b, maintains wiring between electrode support 21b attached to the arm, preventing it from being unwillingly pulled during the execution of daily life actions.

Figure 12A:
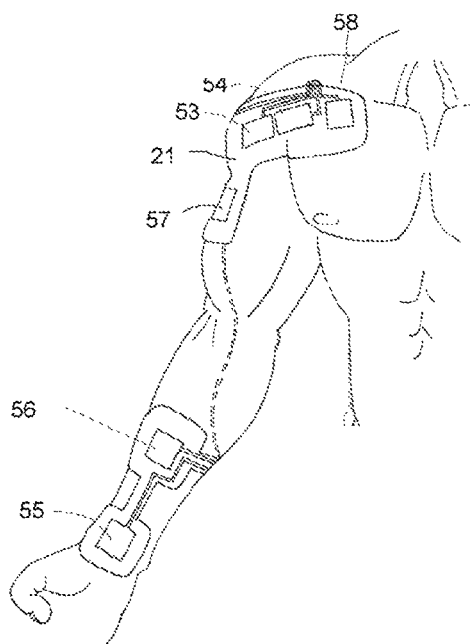
FIG. 12a shows the electrode support montage resulting in one of the actions provided by one of the embodiments of the invention.

FIG. 12a illustrates electrode supports 21 manufactured to embed and correctly place on the body electrodes 53, 54, 55, 56, 57, 58.

Figure 12B:
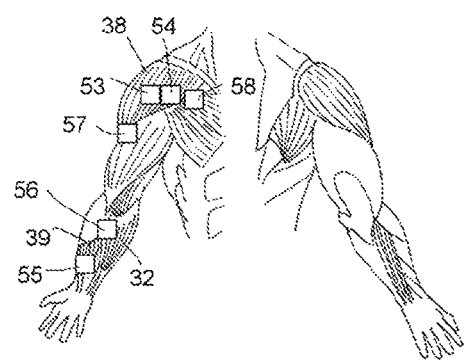
FIG. 12b shows a detailed view of the muscles involved during the electrical stimulation and FIGS. 12c and 12d shows the action produced by the stimulation.

FIG. 12b clarifies the muscles electrically stimulated by the electrodes embedded in support 21. One electrode support 21 is adapted to maintain electrode 55 on the distal portion of the flexor pollicis longus muscle 39, electrode 56 on the ventral portion of the flexor digitorum superficialis muscle 32 (to obtain finger flexion into a palm and thumb grasp). Another electrode support 21 is adapted to maintain electrode 54 on the ventral, distal side of the deltoid 38, electrode 57 on the distal extremity of the deltoid 38 (to obtain arm flexion on the median plane), electrode 53 on the ventral portion of the deltoid 38, electrode 58 on the distal extremity of the pectoralis major 37, under the clavicle (to support and stabilize arm rotation). Electricity is injected through bipolar montages over electrodes 53, 57 and 55, 56 and 54, 58 as to separately stimulate fingers flexors, pectoralis and deltoid muscles.

Electrodes 53, 54, 55, 56, 57, 58 allow stimulation with electrical currents, for example with a rectangular waveform, wherein said waveform has a frequency between 15 and 60 Hz, a pulse width between 150 us and 500 us and a current intensity between 0 and 50 mA.

Figure 12C:
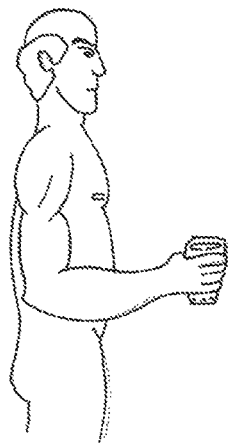
Figure 12D:
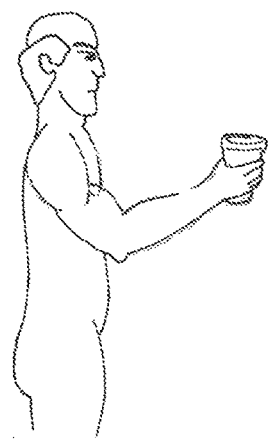

The electrical parameters of currents applied on electrodes 53, 54, 55, 56, 57, 58 are designed to induce a harmonious movement to grasp an object in front of the subject and lift it on its median plane, frontally as shown in FIG. 12c (starting position) and FIG. 12d (final position).

Figure 13:
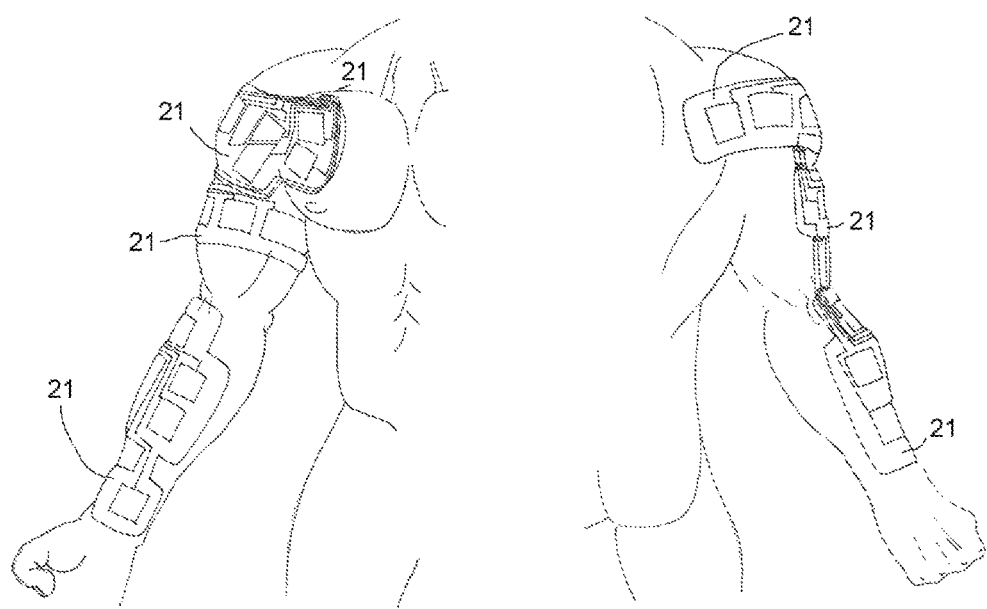
FIG. 13 shows an electrode support configuration for another embodiment of the invention.

FIG. 13 shows several electrodes supports 21 adapted to embed electrodes 1 according to their spatial proximity on the body, in one of the embodiments of the invention.

Embedding the electrodes supports 21 on a surface according to their spatial proximity reduces the number of patches to be applied to the body, thus increasing the ease-of-use of this embodiment of the invention.

Other configurations are possible, for example reducing the number of electrodes to obtain a smaller set of movements.

In a preferred embodiment, illustrated in FIG. 13, the casing 12 embeds the controller unit 3 and the electrical stimulator 2. The controller unit 3 is adapted to receive wirelessly stimulation commands from a master controller 13. The master controller 13 collects and processes data from body tracking system, for example a 3D camera-based tracking system 14.

Figure 14A:
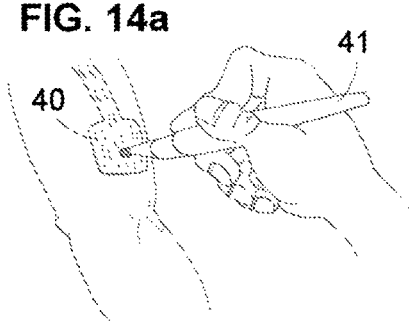
FIG. 14a shows the application of the conductive polymer on the skin.

FIG. 14a shows the application of the conductive polymer 40 on the skin of a user by using a marker 41. Such conductive polymer can be realized for example using silicon-derived fast curing polymers mixed with conductive particles, for example carbon particles, metal particles or other bio-compatible conductive particles or small conductive structures. The polymer can have other properties to facilitate detachment, as for example being washable or degrade autonomously after a defined number of hours. The marker 41 is only one possible way to apply the polymer on the skin, other examples includes brushes or pencils.

Figure 14B:
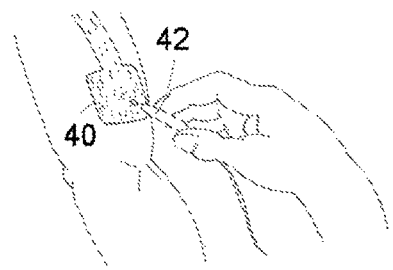
FIG. 14b shows the insertion of a conductive lead into the conductive polymer providing connection to the electrical stimulator.
Figure 14C:
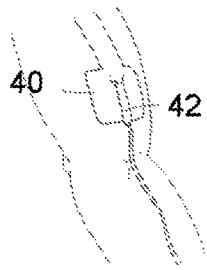
FIG. 14c shows the final cured electrode after the conductive polymer solidified and embedded the lead.

FIG. 14b shows the insertion of a conductive lead 42 into the conductive polymer providing connection to the electrical stimulator. FIG. 14c shows the final cured electrode after the conductive polymer 40 solidified and embedded the lead 42.

Figure 15:
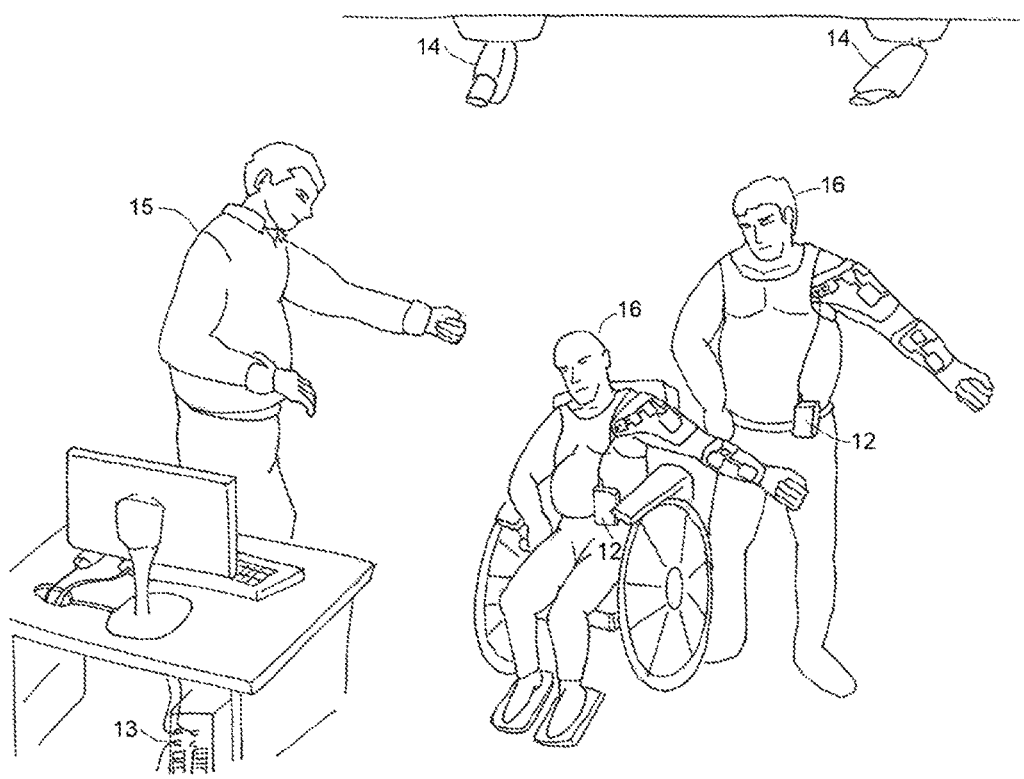
FIG. 15 shows the neuroprosthetic device according to another preferred embodiment of the invention, allowing parallel therapy on several patients through body tracking and electrical stimulation.

In most clinical settings, physical therapy is often performed by groups of patients and one or two physical therapists. Given the complexity of current electrical stimulation devices and the need to program each device for a specific patient, it is currently impossible to perform group exercises interactively. The embodiment illustrated in FIG. 15 enables group physical therapy, for example by replicating the movements of the arm of the therapist on all the patients attending the session.

In a preferred embodiment, movements of one side of the body are replicated on the other side of the body, allowing mirror-like replication of movements.

In alternative embodiments, the body tracking system can be implemented with wearable gyroscopes or accelerometers adapted to communicate with the master controller 13.

The master controller 13 broadcasts stimulation commands to every controller unit 3 in range, replicating the tracked movements of a target user 15 on all other users in range 16.

The invention claimed is:

1. A neuroprosthetic device for restoring daily-life action movements of upper limbs in a patient suffering from motor impairments, the device comprising:
   a plurality of non-invasive electrodes adapted to be fixed on a body of the patient to stimulate at least two separate muscles which participate in an execution of a movement of the upper limb of the body of the patient;
   an electrical stimulation device for providing an electrical current to each of the plurality of electrodes;

a controller device for controlling each of the electrical currents of the electrical stimulation device;

an intention transducing device adapted to generate an input signal for the controller device, the input signal representing an intention of the patient to execute the movement; and a constraining device configured to constraint the movements or immobilize a part of a healthy upper limb of the patient, the constraining device configured to allow sufficient mobility of a hand and a wrist of the healthy upper limb of the patient to operate the intention transducing device, and wherein the controller device controls each of the electrical currents based on the input signal from the intention transducing device to modulate the execution of the movement, so that movements of the upper limb of the body are generated for performing daily-living activities.

2. The neuroprosthetic device of claim 1, wherein the intention transducing device further comprises:

a rotational knob; and a rotational sensor detecting a position of the rotational knob, wherein the input signal of the intention transducing device is generated based on a rotation of the rotational knob by the patient, such that the patient can modulate the execution of the movement.

3. The neuroprosthetic device of claim 1, wherein the intention transducing device further comprises:

a touch sensitive sensor configured to be touched by a healthy limb of the patient, wherein the input signal of the intention transducing device is generated based on at least one of a touch and a slide of a finger of the patient from the healthy limb, such that the patient can modulate the execution of the movement.

4. The neuroprosthetic device of claim 1, wherein the intention transducing device is configured to generate the input signal based on a detector of at least one of neural activity and muscular activity, wherein the detector includes non-invasive electrodes configured to be placed on the body of the patient to record at least one of neural activity and muscular activity, the decoder configured to minimize intrusiveness of the input signal of the intention transducing device.

5. The neuroprosthetic device of claim 1, wherein the intention transducing device is configured to generate the input signal based on a device for tracking movements of a neuroprosthetic device.

6. The neuroprosthetic device of claim 1, wherein the constraining device includes a wearable orthosis, and the intention transducing device is arranged on the wearable orthosis.

7. The neuroprosthetic device of claim 6, wherein the wearable orthosis includes a device for physically displacing the intention transducing device attached away from the healthy hand to unlock a constraint to free the healthy limb, and a displacement device to displace the intention transducing device into a constraining position, to block the use of the healthy limb for uses apart from operating the intention transducing device.

8. The neuroprosthetic device of claim 1, wherein the plurality of non-invasive electrodes are applied to a skin of the user using a marker to release a curing polymer on the skin, the polymer including a silicon-based polymer embedding conductive particles.

9. The neuroprosthetic device of claim 1, wherein each of the plurality of non-invasive electrodes include a patch, the plurality of patches being connected in series, at least one of the patches being connected to the controller device, wherein a patch includes at least one of:

a narrow adhesive section running on a posterior side of a forearm over a line defined by an ulna bone connecting an elbow to a wrist joint of the user;

a narrow adhesive section running on the posterior side of an elbow between a lateral epicondyle and an olecranon of the user;

an elongated adhesive portion running over an acromion; and a narrow adhesive section running from a pectoralis major towards a shoulder adapted to be fixed on a clavicle, wherein a shape of the patch and corresponding wiring are configured to avoid dangling wires and ensure a stability of electrodes on a surface of the skin of the user during complex movements.

10. A method for modulating a movement of a target limb of a target user according to a movement of a limb of a master user, the movement of the target user is generated by a plurality of electrodes mounted on a skin of the limb of the target user, the limb of the master user is tracked by motion detection device, the method comprising the steps of:

detecting a variation of a pose of the limb of the master user tracked by the motion detection device;

detecting a current limb pose of a limb of the target user;

determining a plurality of electrical currents flowing into electrodes that are applied on the limb of the target user, the electrical currents configured to stimulate muscles of the limb to move the limb to achieve a desired limb pose of the limb of the target user based on the variation of the pose of the master user;

applying the plurality of electrical currents to the plurality of electrodes to control the limb of the target user; and controlling electrostimulation parameters including at least one of frequency, pulse width, amplitude, and waveform shape to minimize muscular fatigue of the limb of the target user.

11. The method for modulating movement of claim 10, wherein the step of detecting the current limb pose of the target user, the step of determining the plurality of currents, and the step of applying the plurality of electrical currents is repeated for a plurality of target users to replicate a movement generated by the master user in parallel to the plurality of target users.

12. The method for modulating movement of claim 10, wherein the step of detecting the current limb pose of the target user, the step of determining the plurality of currents, and the step of applying the plurality of electrical currents is repeated on the target user, replicating a movement generated by one side of a body of the target user onto the other side of the body, in a mirror-like manner.

13. A system for modulating a movement of a target limb of a target user according to a movement of a limb of a master user, the system comprising:

a plurality of electrodes configured to be mounted on a skin of the limb of the target user such that the movement of the target user can be generated by the plurality of electrodes;

a controller device configured to control electrical currents for the plurality of electrodes, respectively; and a motion detection device operatively connected to the controller device, configured to track the limb of the master user, wherein the motion detection device is configured to detect and track a variation of a pose of the limb of the master user and to detect a current limb pose of a limb of the target user, wherein the controller device is configured to determine a plurality of electrical currents for the plurality of electrodes, respectively, the electrical currents configured to stimulate muscles of the limb of the target user to move the limb to achieve a desired limb pose of the limb based on the variation of the pose of the master user, is configured to apply the plurality of electrical currents to the plurality of electrodes to control the limb of the target user, and is configured to control electro-stimulation parameters including at least one of frequency, pulse width, amplitude, and waveform shape to minimize muscular fatigue of the limb of the target user.

14. The system for modulating the movement of claim 13, wherein an operation of the motion detector device and the controller device is repeated in parallel to replicate the movement generated by the master user in parallel to a plurality of target users.

15. The system for modulating the movement of claim 13, wherein an operation of the motion detector device and the controller device is repeated in parallel on the target user, to replicate the movement generated by one side of a body of the target user onto another side of the body of the target user, in a mirror-like manner.

16. The neuroprosthetic device of claim 1, further comprising:
a device for immobilizing a healthy side of the body of the patient such that the patient can still operate an input device of the intention transducing device with a healthy limb.

17. The neuroprosthetic device of claim 1, wherein the constraining device and intention transducing device are configured to be arranged on the healthy upper limb.

18. The neuroprosthetic device of claim 1, wherein the constraining device and intention transducing device are part of a same unit.

* * * * *